United States Patent
Mazlish et al.

(10) Patent No.: US 10,610,644 B2
(45) Date of Patent: Apr. 7, 2020

(54) INSULIN DELIVERY METHODS, SYSTEMS AND DEVICES

(71) Applicant: Bigfoot Biomedical, Inc., Milpitas, CA (US)

(72) Inventors: Bryan Mazlish, Palo Alto, CA (US); Lane Desborough, Thousand Oaks, CA (US)

(73) Assignee: Bigfoot Biomedical, Inc., Milpitas, CA (US)

( * ) Notice: Subject to any disclaimer, the term of this patent is extended or adjusted under 35 U.S.C. 154(b) by 183 days.

(21) Appl. No.: 15/870,686

(22) Filed: Jan. 12, 2018

(65) Prior Publication Data
US 2018/0200439 A1    Jul. 19, 2018

Related U.S. Application Data

(60) Provisional application No. 62/560,983, filed on Sep. 20, 2017, provisional application No. 62/446,236, filed on Jan. 13, 2017.

(51) Int. Cl.
*A61M 5/172* (2006.01)
*G16H 20/17* (2018.01)
(Continued)

(52) U.S. Cl.
CPC .......... *A61M 5/1723* (2013.01); *G16H 20/17* (2018.01); *A61B 5/0024* (2013.01);
(Continued)

(58) Field of Classification Search
CPC ............ A61M 5/1723; A61M 5/14244; A61M 5/172; A61M 5/142; A61M 5/14248;
(Continued)

(56) References Cited

U.S. PATENT DOCUMENTS

| 4,464,170 A | 8/1984 | Clemens et al. |
| 6,379,301 B1 | 4/2002 | Worthington et al. |

(Continued)

FOREIGN PATENT DOCUMENTS

| AU | 2015200829 A1 | 3/2015 |
| EP | 2967450 | 1/2016 |

(Continued)

OTHER PUBLICATIONS

David A. Copp, Ravi Gondhalekar, and Joao P. Hespanha, Simultaneous Model Predictive Control and 5 Moving Horizon Estimation for Blood Glucose Regulation in Type 1 Diabetes, Optimal Control Applications and Methods, Wiley InterScience, DOI: 10.1002/oca, pp. 1-15, Oct. 2016.

(Continued)

*Primary Examiner* — Manuel A Mendez
(74) *Attorney, Agent, or Firm* — TraskBritt (57) ABSTRACT

Methods of insulin delivery may include obtaining one or more blood glucose readings from a flash glucose monitor, where the blood glucose readings may be obtained in response to a user invocation of the flash glucose monitor. The method may also include generating multiple insulin delivery profiles of insulin delivery actions over multiple diurnal time segments based on the one or more blood glucose readings. The method may additionally include selecting one of the delivery profiles that is projected to approximate a target blood glucose level, and delivering insulin according to the selected delivery profile. Systems may provide such insulin delivery.

20 Claims, 6 Drawing Sheets

(51) Int. Cl.
*A61M 5/142* (2006.01)
*A61B 5/145* (2006.01)
*A61B 5/00* (2006.01)

(52) U.S. Cl.
CPC ...... *A61B 5/14532* (2013.01); *A61M 5/14244* (2013.01); *A61M 2230/201* (2013.01)

(58) Field of Classification Search
CPC . A61B 5/14532; A61B 5/4839; A61B 5/7275; A61B 5/1495; G06F 19/3418; G06F 19/3456; G06F 19/3468; G06F 19/3475; A61K 38/28; G16H 20/17; G16H 40/63; G16H 50/20
See application file for complete search history.

(56) References Cited

U.S. PATENT DOCUMENTS

| | | | |
|---|---|---|---|
| 6,544,212 B2 | 4/2003 | Galley et al. |
| 6,551,276 B1 | 4/2003 | Mann et al. |
| 6,554,798 B1 | 4/2003 | Mann et al. |
| 6,558,351 B1 | 5/2003 | Steil et al. |
| 6,599,281 B1 | 7/2003 | Struys et al. |
| 6,605,072 B2 | 8/2003 | Struys et al. |
| 6,740,072 B2 | 5/2004 | Starkweather et al. |
| 6,799,149 B2 | 9/2004 | Hartlaub |
| 6,827,702 B2 | 12/2004 | Lebel et al. |
| 6,872,200 B2 | 3/2005 | Mann |
| 6,873,268 B2 | 3/2005 | Lebel et al. |
| 6,936,029 B2 | 8/2005 | Mann |
| 6,979,326 B2 | 12/2005 | Mann et al. |
| 6,997,920 B2 | 2/2006 | Mann et al. |
| 7,025,743 B2 | 4/2006 | Mann et al. |
| 7,060,059 B2 | 6/2006 | Keith et al. |
| 7,066,910 B2 | 6/2006 | Bauhahn et al. |
| 7,109,878 B2 | 9/2006 | Mann et al. |
| 7,133,329 B2 | 11/2006 | Skyggebjerg et al. |
| 7,179,226 B2 | 2/2007 | Crothall et al. |
| 7,204,823 B2 | 4/2007 | Estes et al. |
| 7,220,240 B2 | 5/2007 | Struys et al. |
| 7,267,665 B2 | 9/2007 | Steil et al. |
| 7,354,420 B2 | 4/2008 | Steil et al. |
| 7,402,153 B2 | 7/2008 | Steil et al. |
| 7,404,796 B2 | 7/2008 | Ginsberg |
| 7,491,187 B2 | 2/2009 | Van et al. |
| 7,547,281 B2 | 6/2009 | Hayes et al. |
| 7,569,030 B2 | 8/2009 | Lebel et al. |
| 7,651,845 B2 | 1/2010 | Doyle, III et al. |
| 7,704,226 B2 | 4/2010 | Mueller et al. |
| 7,734,323 B2 | 6/2010 | Blomquist et al. |
| 7,766,829 B2 | 8/2010 | Sloan et al. |
| 7,785,313 B2 | 8/2010 | Mastrototaro |
| 7,806,853 B2 | 10/2010 | Wittmann et al. |
| 7,806,854 B2 | 10/2010 | Damiano et al. |
| 7,815,602 B2 | 10/2010 | Mann et al. |
| 7,819,843 B2 | 10/2010 | Mann et al. |
| 7,850,641 B2 | 12/2010 | Lebel et al. |
| 7,967,812 B2 | 6/2011 | Jasperson et al. |
| 7,976,492 B2 | 7/2011 | Brauker et al. |
| 8,062,249 B2 | 11/2011 | Wilinska et al. |
| 8,088,098 B2 | 1/2012 | Yodfat et al. |
| 8,105,268 B2 | 1/2012 | Lebel et al. |
| 8,152,789 B2 | 4/2012 | Starkweather et al. |
| 8,206,350 B2 | 6/2012 | Mann et al. |
| 8,208,984 B2 | 6/2012 | Blomquist et al. |
| 8,226,556 B2 | 7/2012 | Hayes et al. |
| 8,267,893 B2 | 9/2012 | Moberg et al. |
| 8,273,052 B2 | 9/2012 | Damiano et al. |
| 8,352,011 B2 | 1/2013 | Van et al. |
| 8,417,311 B2 | 4/2013 | Rule |
| 8,439,834 B2 | 5/2013 | Schmelzeisen-Redeker et al. |
| 8,439,897 B2 | 5/2013 | Yodfat et al. |
| 8,454,576 B2 | 6/2013 | Mastrototaro et al. |
| 8,460,231 B2 | 6/2013 | Brauker et al. |
| 8,480,655 B2 | 7/2013 | Jasperson et al. |
| 8,548,544 B2 | 10/2013 | Kircher et al. |
| 8,551,045 B2 | 10/2013 | Sie et al. |
| 8,560,082 B2 | 10/2013 | Wei |
| 8,560,131 B2 | 10/2013 | Haueter et al. |
| 8,562,587 B2 | 10/2013 | Kovatchev et al. |
| 8,579,879 B2 | 11/2013 | Palerm et al. |
| 8,585,591 B2 | 11/2013 | Sloan et al. |
| 8,585,637 B2 | 11/2013 | Wilinska |
| 8,585,638 B2 | 11/2013 | Blomquist |
| 8,615,366 B2 | 12/2013 | Galley et al. |
| 8,694,115 B2 | 4/2014 | Goetz et al. |
| 8,706,691 B2 | 4/2014 | McDaniel et al. |
| 8,718,949 B2 | 5/2014 | Blomquist et al. |
| 8,721,585 B2 | 5/2014 | Brauker et al. |
| 8,727,982 B2 | 5/2014 | Jennewine |
| 8,734,428 B2 | 5/2014 | Blomquist |
| 8,747,315 B2 | 6/2014 | Brauker et al. |
| 8,777,896 B2 | 7/2014 | Starkweather et al. |
| 8,784,369 B2 | 7/2014 | Starkweather et al. |
| 8,784,370 B2 | 7/2014 | Lebel et al. |
| 8,795,224 B2 | 8/2014 | Starkweather et al. |
| 8,876,755 B2 | 11/2014 | Taub et al. |
| 8,945,094 B2 | 2/2015 | Nordh |
| 8,977,504 B2 | 3/2015 | Hovorka |
| 8,992,475 B2 | 3/2015 | Mann et al. |
| 9,056,165 B2 | 6/2015 | Steil et al. |
| 9,320,471 B2 | 4/2016 | Hayes et al. |
| 9,333,298 B2 | 5/2016 | Kim et al. |
| 9,415,157 B2 | 8/2016 | Mann et al. |
| 9,474,855 B2 | 10/2016 | McCann et al. |
| 9,480,796 B2 | 11/2016 | Starkweather et al. |
| 9,486,172 B2 | 11/2016 | Cobelli et al. |
| 9,486,578 B2 | 11/2016 | Finan et al. |
| 2003/0060765 A1 | 3/2003 | Campbell et al. |
| 2003/0114836 A1 | 6/2003 | Estes et al. |
| 2003/0181852 A1 | 9/2003 | Mann et al. |
| 2003/0187525 A1 | 10/2003 | Mann et al. |
| 2003/0191431 A1 | 10/2003 | Mann et al. |
| 2003/0195462 A1 | 10/2003 | Mann et al. |
| 2003/0212364 A1 | 11/2003 | Mann et al. |
| 2005/0171513 A1 | 8/2005 | Mann et al. |
| 2006/0253067 A1 | 11/2006 | Staib et al. |
| 2008/0033357 A1 | 2/2008 | Mann et al. |
| 2008/0097289 A1 | 4/2008 | Steil et al. |
| 2008/0147004 A1 | 6/2008 | Mann et al. |
| 2008/0147050 A1 | 6/2008 | Mann et al. |
| 2008/0183060 A1 | 7/2008 | Steil et al. |
| 2008/0208113 A1 | 8/2008 | Damiano et al. |
| 2008/0269714 A1 | 10/2008 | Mastrototaro et al. |
| 2008/0319384 A1 | 12/2008 | Yodfat et al. |
| 2009/0149728 A1 | 6/2009 | Van et al. |
| 2009/0164239 A1 | 6/2009 | Hayter et al. |
| 2009/0164251 A1 | 6/2009 | Hayter |
| 2010/0082167 A1 | 4/2010 | Haueter et al. |
| 2010/0125241 A1 | 5/2010 | Prud et al. |
| 2010/0137788 A1 | 6/2010 | Braithwaite et al. |
| 2010/0138197 A1 | 6/2010 | Sher |
| 2010/0249561 A1 | 9/2010 | Patek et al. |
| 2010/0256466 A1 | 10/2010 | Shekalim et al. |
| 2010/0262117 A1 | 10/2010 | Magni et al. |
| 2011/0015511 A1 | 1/2011 | Bousamra et al. |
| 2011/0208156 A1 | 8/2011 | Doyle et al. |
| 2012/0123234 A1 | 5/2012 | Atlas et al. |
| 2012/0172694 A1 | 7/2012 | Desborough et al. |
| 2012/0227737 A1 | 9/2012 | Mastrototaro et al. |
| 2012/0245556 A1 | 9/2012 | Kovatchev et al. |
| 2012/0246106 A1 | 9/2012 | Atlas et al. |
| 2013/0102867 A1 | 4/2013 | Desborough et al. |
| 2013/0231642 A1 | 9/2013 | Doyle et al. |
| 2013/0245547 A1 | 9/2013 | El-Khatib et al. |
| 2013/0338629 A1 | 12/2013 | Agrawal et al. |
| 2013/0338630 A1 | 12/2013 | Agrawal et al. |
| 2013/0345663 A1 | 12/2013 | Agrawal et al. |
| 2014/0005633 A1 | 1/2014 | Finan |
| 2014/0066884 A1 | 3/2014 | Keenan et al. |
| 2014/0066887 A1 | 3/2014 | Mastrototaro et al. |
| 2014/0066888 A1 | 3/2014 | Parikh et al. |
| 2014/0066889 A1 | 3/2014 | Grosman et al. |
| 2014/0180240 A1 | 6/2014 | Finan et al. |

(56) References Cited

U.S. PATENT DOCUMENTS

| | | |
|---|---|---|
| 2014/0276553 A1 | 9/2014 | Rosinko et al. |
| 2014/0276554 A1 | 9/2014 | Finan et al. |
| 2014/0276555 A1 | 9/2014 | Morales |
| 2014/0309615 A1 | 10/2014 | Mazlish |
| 2014/0350369 A1 | 11/2014 | Budiman et al. |
| 2015/0045767 A1 | 2/2015 | Kamen et al. |
| 2015/0073337 A1 | 3/2015 | Saint et al. |
| 2015/0164343 A1 | 6/2015 | Huang et al. |
| 2015/0238694 A1 | 8/2015 | Steil et al. |
| 2015/0289823 A1 | 10/2015 | Rack-Gomer et al. |
| 2015/0314062 A1 | 11/2015 | Blomquist et al. |
| 2015/0328402 A1 | 11/2015 | Nogueira et al. |
| 2016/0030669 A1 | 2/2016 | Harris et al. |
| 2016/0038673 A1 | 2/2016 | Morales |
| 2016/0082187 A1 | 3/2016 | Schaible et al. |
| 2016/0082188 A1 | 3/2016 | Blomquist et al. |
| 2016/0158438 A1 | 6/2016 | Monirabbasi et al. |
| 2016/0162662 A1 | 6/2016 | Monirabbasi et al. |
| 2016/0213841 A1 | 7/2016 | Geismar et al. |
| 2016/0256629 A1 | 9/2016 | Grosman et al. |
| 2016/0317743 A1 | 11/2016 | Estes |
| 2017/0049386 A1 | 2/2017 | Abraham et al. |
| 2017/0182248 A1 | 6/2017 | Rosinko |
| 2017/0332952 A1 | 11/2017 | Desborough et al. |

FOREIGN PATENT DOCUMENTS

| | | |
|---|---|---|
| JP | 2008-545454 A | 12/2008 |
| JP | 2010-531678 A | 9/2010 |
| WO | 2006/124716 A3 | 3/2007 |
| WO | 2008/057384 A3 | 9/2008 |
| WO | 2008/157780 A1 | 12/2008 |
| WO | 2010/089307 A1 | 8/2010 |
| WO | 2011/030343 A1 | 3/2011 |
| WO | 2014/149535 A1 | 9/2014 |
| WO | 2015/187738 A1 | 12/2015 |
| WO | 2017/027459 A1 | 2/2017 |

OTHER PUBLICATIONS

Dassau and Associates, 12-Week 24/7 Ambulatory Artificial Pancreas With Weekly Adaptation of Insulin Delivery Settings: Effect on Hemoglobin A1C and Hypoglycemia, Diabetes Care, Oct. 13, 2017.

Guy A. Dumont, Feedback Control for Clinicians, Springer Science+ Media, Apr. 12, 2013, New York.

Fischer et al., In Vivo Comparison of Different Algorithms for the Artificial Beta-Cell, Artificial Organs, 9(2), International Society for Artificial Organs, May 1985, New York.

E. Salzsieder, G. Albrecht, E. Jutzi, and U. Fischer, Estimation of Individually Adapted Control Parameters or an Artificial Beta Cell, Biomedica Biochimica Acta. 43(5) pp. 585-596, May 1984.

Michele Schiavon, Chiara Dalla Man, Yogish C. Kudva, Ananda Basu, and Claudio Cobelli, Quantitative Estimation of Insulin Sensitivity in Type 1 Diabetic Subjects Wearing a Sensor-Augmented Insulin Pump, Diabetes Care, vol. 37, pp. 1216-1223, May 2014.

Samuel Vozeh and Jean-Louis Steimer, Feedback Control Methods for Drug Dosage Optimisation, Concepts, Classification and Clinical Application, Clinical Pharmacokinetics, 10(6), pp. 457-476, Nov.-Dec. 1985.

Written Opinion of the International Searching Authority for PCT Application No. PCT/US2018/013595, dated Jun. 8, 2018, 7 pages.

International Search Report for PCT Application No. PCT/US2018/013595, dated Jun. 8, 2018, 4 pages.

FIG. 6B

INSULIN DELIVERY METHODS, SYSTEMS AND DEVICES

CROSS-REFERENCE TO RELATED APPLICATION

This application claims the benefit under 35 U.S.C. § 119(e) of U.S. Provisional Patent Application Ser. No. 62/560,983, filed Sep. 20, 2017, and U.S. Provisional Patent Application Ser. No. 62/446,236, filed Jan. 13, 2017, the disclosure of each of which is hereby incorporated herein in its entirety by this reference.

TECHNICAL FIELD

This disclosure relates to insulin delivery based on glucose monitoring.

BACKGROUND

People with Type I, Type II, or gestational diabetes must track their blood glucose levels and sometimes treat their condition to maintain appropriate blood glucose levels. Control of diabetes can include the monitoring of blood glucose levels using a variety of devices. Examples of such devices include blood glucose monitors (BGM), continuous glucose monitors (CGM), and sometimes flash glucose monitors. People with Type I, and some people with Type II or gestational diabetes, require insulin or an analog thereof. Because it cannot be taken orally, insulin is injected with a syringe or delivered subcutaneously by an external infusion pump. However, each person responds to insulin in a slightly different way. Furthermore, blood glucose levels can vary at different times of the day.

In addition to variations in blood glucose levels, other factors associated with the treatment of diabetes can also vary. For example, an insulin sensitivity factor (ISF) and a carbohydrate to insulin ratio (CR) can vary from person to person and at various points in time.

To account for such variations, some systems personalize one or more of these factors. However, such personalization sometime relies on the use of a CGM for automatic and repeated data points of blood glucose levels.

The subject matter claimed in the present disclosure is not limited to embodiments that solve any disadvantages or that operate only in environments such as those described above. Rather, this background is only provided to illustrate one example technology area where some embodiments described in the present disclosure may be practiced.

BRIEF SUMMARY

Medication delivery systems, methods, and devices provided herein include at least a flash blood glucose monitoring device and a control device (e.g., a smartphone having an installed app) to personalize insulin delivery for a person with diabetes (PWD). In some cases, the control device can serve as the primary user interface for providing blood glucose level information to a user. In some cases, methods, devices, and systems provided herein can include an insulin delivery device (e.g., an insulin pump, a smart insulin pen, a connected dose-capture cap for an insulin pen, etc.) in communication with or part of the blood glucose monitoring device and/or the display device. In some cases, the control device may be configured to monitor or otherwise obtain blood glucose levels via the flash blood glucose monitor and personalize the delivery of insulin based on the information from the flash blood glucose monitor.

One or more embodiments of the present disclosure may include a method of insulin delivery. The method may include obtaining one or more blood glucose readings from a flash glucose monitor (e.g., where the blood glucose readings may be obtained from the in response to a user invocation of the flash glucose monitor). The method may also include generating multiple insulin delivery profiles of insulin delivery actions over multiple diurnal time segments based on the one or more blood glucose readings. The method may additionally include selecting one of the delivery profiles that is projected to approximate a target blood glucose level, and providing the selected delivery profile to be utilized with an insulin delivery device to deliver the selected delivery profile to the user. In some embodiments, the method may include delivering insulin according to the selected delivery profile.

One or more embodiments of the present disclosure may include an insulin delivery system comprising an insulin delivery device configured to deliver insulin to a user, a flash glucose monitor configured to obtain one or more blood glucose readings from the user, and a controller configured to perform or control performance of operations. The operations comprising obtaining one or more blood glucose readings from the flash glucose monitor, generating a plurality of insulin delivery profiles of insulin delivery actions over a plurality of diurnal time segments based on the one or more blood glucose readings, selecting one of the delivery profiles that is projected to approximate a target blood glucose level; and providing the selected delivery profile to be utilized with the insulin delivery device to deliver at least a portion of the selected delivery profile to the user.

The details of one or more implementations of various embodiments are set forth in the accompanying drawings and the description below. Other features, objects, and advantages of the various embodiments will be apparent from the description and drawings, and from the claims.

It is to be understood that both the foregoing general description and the following detailed description are merely examples and explanatory and are not restrictive of the claims.

BRIEF DESCRIPTION OF THE DRAWINGS

Example embodiments will be described and explained with additional specificity and detail through the use of the accompanying drawings in which.

DETAILED DESCRIPTION

The present disclosure may relate to, inter alia, insulin delivery based on user-initiated glucose readings. For example, a diabetes management system may include a control device, an insulin pump, and a flash glucose monitor. A flash glucose monitor may include any device configured to be in a position to obtain blood glucose readings but take those readings or report those readings upon a user initiated action. For example, a user may submit a query or request to the flash glucose monitor flash glucose monitor (e.g., by invoking a button, tapping the flash glucose monitor, invoking a feature on the control device to send a signal to the flash glucose monitor, etc.) to either perform a reading of a current blood glucose level and/or to report any stored blood glucose levels. In some cases, a flash glucose monitor may be configured to only take a reading of the blood glucose levels of a PWD based on receiving a command to do so. In other cases, a flash glucose monitor may be configured to periodically take readings of the blood glucose levels and store those readings, and may report, display, or otherwise provide those readings based on receiving such a command.

Personalizing the delivery of insulin may include any approach of adjusting one or more factors associated with insulin delivery based on properties of the PWD. For example, such personalization may include generating multiple insulin delivery profiles and projected blood glucose levels for each of the insulin delivery profiles, and selecting the profile that closely tracks towards a target blood glucose level. In addition, factors that contribute to the predicted blood glucose levels (e.g., insulin sensitivity factor (ISF), carbohydrate to insulin ratio (CR), etc.) may also be personalized over time. Examples of such personalization is described in greater detail in U.S. application Ser. No. 15/601,282, the disclosure of which is hereby incorporated herein in its entirety by this reference.

Methods and systems provided herein can use information from a flash glucose monitor to have up-to-date blood glucose data (e.g., multiple blood glucose data points each hour) for the PWD in order to determine how to adjust basal insulin delivery rates (referred to as "baseline basal rate" or BBR). In some cases, methods and systems provided herein can use blood glucose data from both a flash glucose monitor and one or more BGMs to validate readings of the flash glucose monitor. Methods and systems provided herein can be part of a hybrid closed loop system (for example, where basal rates can be adjusted automatically and the PWD can manually enter or deliver a bolus). In some cases, methods and system provided herein can be part of a fully closed loop system (for example, where basal rates can be adjusted automatically and boluses can be delivered automatically). In some cases, "up to date" may mean less than 1 hour old, less than 30 minutes old, or less than 15 minutes old, and "stale" may mean not up to date.

Methods and systems provided herein can use a model to predict multiple future blood glucose levels for multiple different basal insulin delivery profiles or basal insulin delivery rates, and select one of the basal insulin delivery profiles or basal insulin delivery rates based on prediction of which profile or rate will approximate a target blood glucose level, or more specifically, select the profile that minimizes the differences between the predicted future blood glucose values and one or more target blood glucose values. In some cases, the profile that minimizes, lessens, or lowers variations from one or more target blood glucose levels in the future may be selected. The selected basal profile can then be delivered to the PWD at least until a process of evaluating different basal insulin delivery profiles or rates is repeated. The different basal insulin delivery profiles or rates for each evaluation process can be generated using any suitable technique or techniques. In some cases, multiple profiles or delivery rates are generated using one or more user-specific dosage parameters. In some cases, one or more user-specific dosage parameters can be entered by a user, calculated by information entered by a user, and/or calculated by monitoring data generated from the PWD (e.g., monitoring insulin delivery rates and blood glucose data while the PWD is using a pump in an open loop mode). In some cases, methods and systems provided herein can modify user-specific dosage parameters over time based on one or more selected basal insulin delivery profiles or rates and/or other data obtained from the PWD. In some cases, the user-specific dosage parameters can be dosage parameters that are commonly used in the treatment of diabetes, such as average total daily insulin, total daily basal (TDB) insulin, average basal rate, insulin sensitivity factor (ISF), and carbohydrate-to-insulin ratio (CR). For example, in some cases, a PWD's average basal rate can be used to calculate multiple different basal insulin delivery profiles based on multiples or fractions of the average basal rate used over different intervals of time. In some cases, methods and systems provided herein can use time-interval-specific user-specific dosage parameters (e.g., a time-interval-specific baseline basal rate). In some cases, methods and systems provided herein can make adjustments to time-interval-specific user-specific dosage parameters for each time interval for where a delivered basal rate varies from a baseline basal rate for that time interval. In some cases, user-specific dosage parameters are specific for time intervals of two hours or less, one hour or less, thirty minutes or less, or fifteen minutes or less. For example, in some cases, methods and systems provided herein can store a baseline basal rate (BBR) for the hour between 1 PM and 2 PM, and can adjust the BBR for that hour up if the method or system delivers more basal insulin during that time period and adjust the BBR down if the method or system delivers less basal insulin during that time period. In some cases, adjustments to user-specific dosage parameters can be based on a threshold variation and/or can be limited to prevent excessive adjustments to user-specific dosage parameters. For example, in some cases, a daily adjustment to a user-specific dosage parameter can be limited to less than 10%, less than 5%, less than 3%, less than 2%, or to about 1%. In some cases, an adjustment to a baseline basal rate is less than a difference between the amount of basal insulin actually delivered and the baseline basal for a specific period of time (e.g., if a baseline basal rate is 1 Unit of insulin ("U")/hour and systems or methods provided herein actually delivered 2U for the previous hour, the adjustment to any baseline basal rate based on that difference would be less than 1U/hour).

Methods and systems provided herein can use any appropriate model to predict multiple future blood glucose values. In some cases, predictive models can use one or more current or recent blood glucose measurements (e.g., from the flash glucose monitor), estimates of rates of change of blood glucose levels, an estimation of unacted carbohydrates, and/or an estimation of unacted insulin. In some cases, predictive models can use one or more user-specific dosage parameters in predicting multiple blood glucose values over a future time interval for multiple different basal insulin delivery profiles or rates over that same future time interval. That future time interval can be at least two hours, at least three hours, or at least four hours, at least five hours, etc. User-specific dosage parameters, which can be time-interval-specific, can also be used in determining an estimation of unacted carbohydrates and/or an estimation of unacted insulin. In some cases, an estimation of unacted carbohydrates and/or an estimation of unacted insulin can use a simple decay function. In some cases, an estimate of unacted insulin can be determined using an Insulin On Board (IOB) calculation, which are common in diabetes treatment. In some cases, an IOB calculation used in a predictive model used in methods and systems provided herein can consider insulin delivered to the PWD during the delivery of a bolus. In some cases, the IOB calculation can additionally add or subtract to the IOB based on changes to the basal insulin delivery rate from a baseline basal rate. In some cases, an estimate of unacted carbohydrates can be determined using a Carbohydrates On Board (COB) calculation, which can be based on a decay function and announced meals. In some cases, predictive models used in methods and systems provided herein can also consider the non-carbohydrate components of a meal. In some cases, methods and systems provided herein can infer an amount of carbohydrates from an unannounced meal due to a spike in up-to-date blood glucose data. In some cases, predictive models used in methods and systems provided herein can additionally consider additional health data or inputs, which may indicate that the PWD is sick, exercising, experiencing menses, or some other condition that may alter the PWD's reaction to insulin and/or carbohydrates. In some cases, at least an IOB, a COB, an insulin sensitivity factor (ISF), and a carbohydrate-to-insulin ratio (CR) are used to predict future blood glucose values for each evaluated basal insulin delivery profile or rate.

Methods and systems provided herein can set one or more blood glucose targets using any suitable technique. In some cases, a blood glucose target can be fixed, either by a user or pre-programmed into the system. In some cases, the target blood glucose level can be time interval specific (e.g., based on diurnal time segments). In some cases, a user can temporarily or permanently adjust the target blood glucose level. In some cases, methods and systems provided herein can make adjustments to target blood glucose levels in order to minimize, lessen, or lower a risk of the PWD having a hypoglycemic event. In some cases, methods and systems provided herein can make adjustments to target blood glucose levels in order to minimize, lessen, or lower a risk of the PWD having a hyperglycemic event. For example, in some cases, methods and systems provided herein can analyze a variability of blood glucose data for the PWD and select a blood glucose target based on that variability. In some cases, methods and systems provided herein can analyze the variability of blood glucose data for diurnal time segments and adjust the blood glucose target individually for each diurnal time segment. For example, some PWDs may have a lower blood glucose variability at night, thus systems and methods provided herein can reduce blood glucose targets for nighttime diurnal time segments because of the lower probability that a lower blood glucose target would result in a hypoglycemic event during those lower variability time segments. Reducing the blood glucose target for diurnal time segments having a lower variability can reduce the amount of hyperglycemic events for the PWD. In some cases, PWDs may have a larger variability around the times of day when they typically have meals (e.g., due to mismatches in timing and amounts of insulin boluses and carbohydrate ingestion), thus methods and systems provided herein can detect diurnal time segments having a wider range of variability and increase the blood glucose target for those time periods to reduce the probability of a hypoglycemic event during those time periods. In some cases, methods and systems provided herein can analyze the variability of blood glucose data for specific days of the week and/or based on other physiological patterns and adjust the blood glucose targets for that individual based on the specific day of the week or based on other physiological patterns. For example, a PWD may have certain days of the week when they exercise and/or PWD may have different insulin needs based on a menses cycle.

Methods and systems provided herein can evaluate each basal insulin delivery profile or rate to select the profile or rate that minimizes a variation from the one or more blood glucose targets using any appropriate method. In some cases, methods and systems provided herein can use a cost function to evaluate differences between the predicted blood glucose values for each basal insulin delivery profile or rate and blood glucose targets, potentially specified for a diurnal time segment. Methods and systems provided herein can then select a basal profile or rate that produces the lowest cost function value. Methods and systems provided herein can use any suitable cost function. In some cases, cost functions can sum the absolute value of the difference between each predicted blood glucose value and each blood glucose target. In some cases, cost functions used in methods and systems provided herein can use square of the difference. In some cases, cost functions used in methods and systems provided herein can assign a higher cost to blood glucose values below the blood glucose target in order reduce the risk of a hypoglycemic event. In some cases, the cost function can include a summation of the absolute values of a plurality of predicted deviations, squared deviations, log squared deviations, or a combination thereof In some cases, a cost function can include variables unrelated to the predicted blood glucose values. For example, a cost function can include a penalty for profiles that do not deliver 100% of the BBR, thus adding a slight preference to use 100% of BBR. In some cases, methods and systems provided herein can include a cost function that provides a slight preference to keep the existing basal modification for every other interval (e.g., a second 15 minute segment), which could reduce the variability in basal insulin delivery rates in typical situations, but allow for more critical adjustments.

Methods and systems provided herein can store a plurality of user-specific dosage parameters (e.g., BBR, CR, and ISF) as different values for a plurality of different diurnal time segments. As used herein, "diurnal time segments" periods of time during each day (e.g., a 24-hour time period), such that the methods and systems will repeat use of each diurnal-specific user-specific dosage parameter during the same time on subsequent days if a stored diurnal-specific user-specific dosage parameter is not modified or changed, thus the use of the stored diurnal-specific user-specific dosage parameter will wrap each day. Methods and systems provided herein, however, can be adapted to make daily (or more or less frequent) adjustments to each diurnal-specific user-specific dosage parameter based on the operation of the system. Methods and systems provided herein may additionally store settings or adjustments for specific days of the week or for other repeating cycles.

After a basal insulin delivery profile or rate is selected, methods and systems provided herein can include the delivery of basal insulin to the PWD according to the selected basal insulin profile or rate for any suitable period of time. In some cases, methods and systems provided herein may supply basal insulin according to the selected basal insulin delivery profile or rate for a predetermined amount of time that may be less than the time interval of the evaluated basal insulin delivery profiles or rates. For example, methods and systems provided herein may analyze projected blood glucose values for basal insulin delivery profiles or rates that last over the next four hours but repeat the process of selecting a new basal insulin delivery profile or rate every fifteen minutes. In some cases, methods and systems provided herein can delay or suspend basal insulin delivery during the delivery of a bolus, which can be triggered by a user requesting a bolus.

In some cases, the use of a flash glucose monitor may impact the operation and/or use of the closed loop insulin delivery adjustments as described above. For example, in some cases, if the flash glucose monitor has not been invoked by the user for a certain duration of time, a diabetes management system can transition out of a closed-loop system that adjusts the amount of insulin delivered and into an open-loop system that delivers the BBR. For example, rather than predicting profiles and delivering 0×, 1×, or 2× the BBR, the diabetes management system may stop predicting and only deliver the BBR until the user invokes the flash glucose monitor and the diabetes management system has additional blood glucose readings on which to base predictions of future blood glucose levels. Such a duration of time may include thirty minutes, one hour, two hours, etc.

In some cases, if operating in an open-looped mode (e.g., delivering the BBR without personalization to deliver 0×, 1×, 2×, or 3× the BBR), the user invoking the flash glucose monitor may cause the diabetes management system to transition into a closed-loop mode. For example, the diabetes management system may use the recent blood glucose readings from the flash glucose monitor to predict future blood glucose levels based on various delivery profiles and may select the delivery profile that most closely matches the target blood glucose level. In these and other embodiments, if the flash glucose monitor delivers multiple historical blood glucose readings, the diabetes management system may use any number of those readings in predicting the future blood glucose levels and/or in generating the delivery profiles.

In some cases, for periods of time in which the diabetes management system is missing blood glucose levels because the user has not invoked the flash glucose monitor, such diurnal time segments may not be used in personalizing the time-interval-specific user-specific dosage parameters. For example, if the flash glucose monitor has not been invoked for two hours, the ISF, CR, and/or other time-interval-specific user-specific dosage parameters for those two hours may not be adjusted or modified for future days during those two hours. Additionally or alternatively, for diurnal time segments in which the diabetes management system transitioned out of the closed-loop mode and into the open loop mode (e.g., only delivering the BBR), the system may or may not adjust the time-interval-specific user-specific dosage parameters for those diurnal time segments.

In some cases, the diabetes management system can adjust the diurnal time segment size the system uses for analysis and/or the frequency with which the system generates new delivery profiles based on the frequency with which a user invokes the flash glucose monitor. For example, the diabetes management system may generate new delivery profiles every fifteen minutes initially, and based on the user invoking the flash glucose monitor every thirty minutes, the system may change to generate new delivery profiles every thirty minutes.

As used herein, "basal insulin delivery" has its normal and customary meaning within the art of the treatment of diabetes. Although basal rates are expressed as a continuous supply of insulin over time, basal insulin delivery may constitute multiple discrete deliveries of insulin at regular or irregular intervals. In some cases, methods and systems provided herein may only be able to deliver insulin in discrete fractions of a unit. For example, some insulin delivery devices can only deliver insulin in a dose that are an integer multiple of 0.05 units or 0.1 units. In some cases, a delivery of basal insulin can include a delivery of insulin at predetermined time intervals less than or equal to fifteen minutes apart or less, ten minutes apart or less, or five minutes apart or less. In some cases, the time interval between discrete basal insulin deliveries can be determined based on the basal insulin delivery rate (e.g., a basal rate of 1.0 units/hour might result in the delivery of 0.1 units every six minutes). As used herein, the term "bolus" has its normal and customary meaning with the art of the treatment of diabetes, and can refer to a bolus delivered in order to counteract a meal (i.e., a meal-time bolus) and/or to correct for elevated blood glucose levels (i.e., a correction bolus).

Methods and systems provided herein can in some cases include multiple delivery modes. In some cases, methods and systems provided herein can monitor the presence of blood glucose using one or more blood glucose measuring devices or methods, control or monitor the dispensation of medicine, and determine and/or update the user-specific dosage parameters regardless of the operating mode. For example, possible operating modes could include closed-loop or hybrid closed-loop modes that automatically adjust basal rates based on flash glucose monitoring data and other user-specific dosage parameters (e.g., baseline basal rate (BBR), insulin sensitivity factor (ISF), and carbohydrate-to-insulin ratio (CR)), modes that can use blood glucose monitor (BGM) data to update user-specific dosage parameters (e.g., BBRs, ISFs, and CRs) for different time blocks over longer periods of time, manual modes that require a patient to manually control the therapy program using an insulin pump, and advisory modes that recommend dosages for a PWD to inject using an insulin pen or syringe. By determining optimized control parameters that work across delivery modes, systems and methods provided herein can provide superior analyte control even when a PWD switches to a different delivery mode. For example, methods and systems provided herein may be forced to switch away from a hybrid closed-loop delivery mode that adjusts basal insulin delivery away from a BBR if a flash glucose monitor malfunctions, the user has not invoked the flash glucose monitor for an extended period of time, or the system otherwise loses access to blood glucose level data. In some cases, data can be collected when the system is in an advisory or manual mode to optimize control parameters in preparation for a PWD to switch to a hybrid closed loop system (e.g., in preparation for a PWD to start use of a flash glucose monitor (flash glucose monitor) and/or an insulin pump).

Methods and systems provided herein can include an insulin pump and at least one blood glucose measurement device in communication with the insulin pump. In some cases, the blood glucose measurement device can be a flash glucose monitor adapted to provide blood glucose measurements when invoked by a user. In some cases, methods and systems provided herein include a flash glucose monitor adapted to capture and/or store blood glucose measurements at least every five minutes, ten minutes, fifteen minutes, or any other periodic interval. Methods and systems provided herein additionally include a control device adapted to determine an amount of basal insulin for delivery to a PWD and memory to store multiple user-specific dosage parameters. In some cases, the control device can be part of an insulin pump. In some cases, the control device can be part of a remote device, which can communicate wirelessly with an insulin pump. In some cases, the control device can communicate wirelessly with a flash glucose monitor. In some cases, methods and systems provided herein can additionally include a user interface for displaying data and/or receiving user commands, which can be included on any component of a system provided herein. In some cases, the user interface can be part of smartphone. In some cases, a user can input information on the user interface to trigger methods and systems provided herein to deliver a bolus of insulin. In some cases, methods and systems provided herein can use a blood glucose meter adapted to use test strip as a blood glucose measurement device. In some cases, methods and systems provided herein can additionally include an insulin pen, which can optionally communicate wirelessly with the control device.

Figure 1:
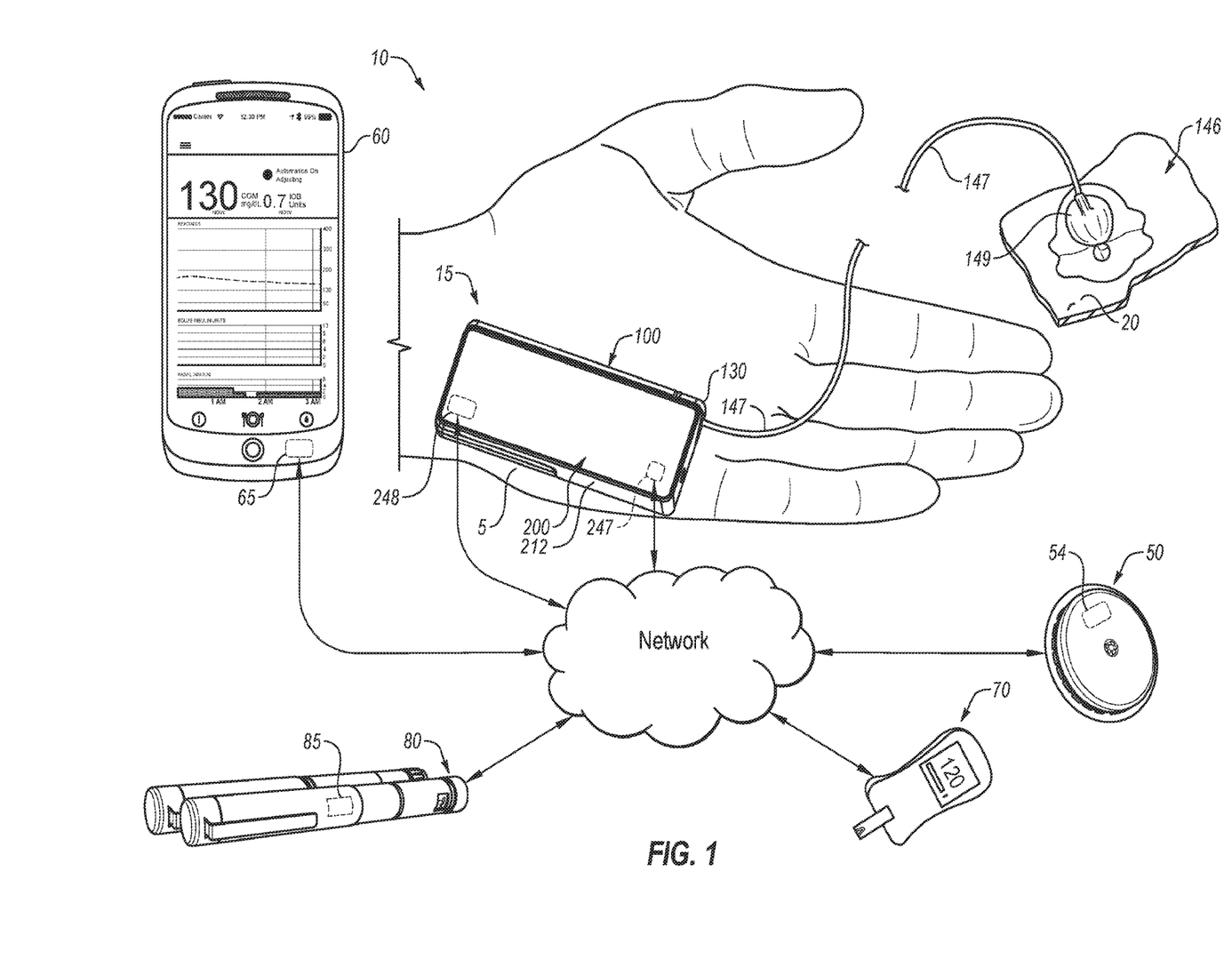
FIG. 1 provides an example system to provide insulin delivery based on user-initiated glucose readings.

FIG. 1 provides an example diabetes management system 10, in accordance with one or more embodiments of the present disclosure. The system 10 may include a pump assembly 15 for providing insulin and a flash glucose monitor 50. As shown, the flash glucose monitor 50 is in wireless communication with pump assembly 15. In some cases, a flash glucose monitor can be in wired communication with pump assembly 15. In some cases not shown, a flash glucose monitor can be incorporated into an insulin pump assembly or other insulin delivery device. As shown, pump assembly 15 can include a reusable pump controller 200 that forms part of the pump assembly 15. In some cases, reusable pump controller 200 is adapted to determine one or more basal delivery rates. In some cases, the flash glucose monitor 50 can act as a controller adapted to communicate basal delivery rates to pump assembly 15.

Pump assembly 15, as shown, can include reusable pump controller 200 and a disposable pump 100, which can contain a reservoir for retaining insulin. A drive system for pushing insulin out of the reservoir can be included in either the disposable pump 100 or the reusable pump controller 200 in a controller housing 212. Reusable pump controller 200 can include a wireless communication device 247, which can be adapted to communicate with a wireless communication device 54 of flash glucose monitor 50 and other diabetes devices in the system 10, such as those discussed below. In some cases, pump assembly 15 can be sized to fit within a palm of a hand 5. Pump assembly 15 can include an infusion set 146. Infusion set 146 can include a flexible tube 147 that extends from the disposable pump 100 to a subcutaneous cannula 149 that may be retained by a skin adhesive patch (not shown) that secures the subcutaneous cannula 149 to the infusion site. The skin adhesive patch can retain the subcutaneous cannula 149 in fluid communication with the tissue or vasculature of the PWD so that the medicine dispensed through flexible tube 147 passes through the subcutaneous cannula 149 and into the PWD's body. Cap device 130 can provide fluid communication between an output end of an insulin cartridge (not shown) and flexible tube 147 of infusion set 146. Although pump assembly 15 is depicted as a two-part insulin pump, one piece insulin pumps are also contemplated. Additionally, insulin pump assemblies used in methods and systems provided herein can alternatively be a patch pump.

Flash glucose monitor 50 (e.g., a glucose monitoring device) can include a housing, a wireless communication device 54, and a sensor shaft (not shown). The wireless communication device 54 can be contained within the housing and the sensor shaft can extend outward from the housing. In use, the sensor shaft can penetrate the skin 20 of a user to make measurements indicative of the PWD's blood glucose level or the like. In some cases, the sensor shaft can measure glucose or another analyte in interstitial fluid or in another fluid and correlate that to blood glucose levels. In some cases, the flash glucose monitor 50 may invoke the sensor shaft and obtain a reading of the blood glucose levels based on the PWD invoking the flash glucose monitor 50. Additionally or alternatively, the flash glucose monitor 50 may periodically store blood glucose readings and may provide those stored readings when the flash glucose monitor 50 is invoked by the PWD. In response to the invocation of the flash glucose monitor 50, the flash glucose monitor 50 can employ the wireless communication device 54 to transmit data to a corresponding wireless communication device 247 housed in the pump assembly 15. In some cases, the flash glucose monitor 50 may include a circuit that permits sensor signals (e.g., data from the sensor shaft) to be communicated to the wireless communication device 54. The wireless communication device 54 can transfer the collected data to reusable pump controller 200 (e.g., by wireless communication to the wireless communication device 247). Additionally or alternatively, the system 10 may include another glucose monitoring device that may utilize any of a variety of methods of obtaining information indicative of a PWD's blood glucose levels and transferring that information to reusable pump controller 200. For example, an alternative monitoring device may employ a micropore system in which a laser porator creates tiny holes in the uppermost layer of a PWD's skin, through which interstitial glucose is measured using a patch. In the alternative, the monitoring device can use iontophoretic methods to non-invasively extract interstitial glucose for measurement. In other examples, the monitoring device can include non-invasive detection systems that employ near IR, ultrasound or spectroscopy, and particular implementations of glucose-sensing contact lenses. In other examples, the monitoring device can detect glucose levels using equilibrium fluorescence detectors (e.g., sensors including a diboronic acid receptor attached to a fluorophore). Furthermore, it should be understood that in some alternative implementations, the flash glucose monitor 50 can be in communication with reusable pump controller 200 or another computing device via a wired connection.

In some cases, the flash glucose monitor 50 can be adapted to provide blood glucose measurements for a PWD when in use for the PWD at regular or irregular time intervals. In some cases, the flash glucose monitor 50 can detect blood glucose measurements at least every thirty minutes, at least every fifteen minutes, at least every ten minutes, at least every five minutes, about every minute, about every thirty seconds, about every fifteen seconds, about every ten seconds, about every five seconds, or about every second, etc. In some cases, the flash glucose monitor 50 can itself determine a basal delivery rate using methods provided herein and communicate that basal rate to the pump assembly 15. In some cases, the flash glucose monitor 50 can transmit blood glucose measurement data to reusable pump controller 200 and reusable pump controller 200 can use methods provided herein to determine a basal delivery rate. In some cases, a remote controller can receive glucose data from the flash glucose monitor 50, determine a basal delivery rate using methods provided herein, and communicate the basal rate to pump assembly 15.

Figure 4A:
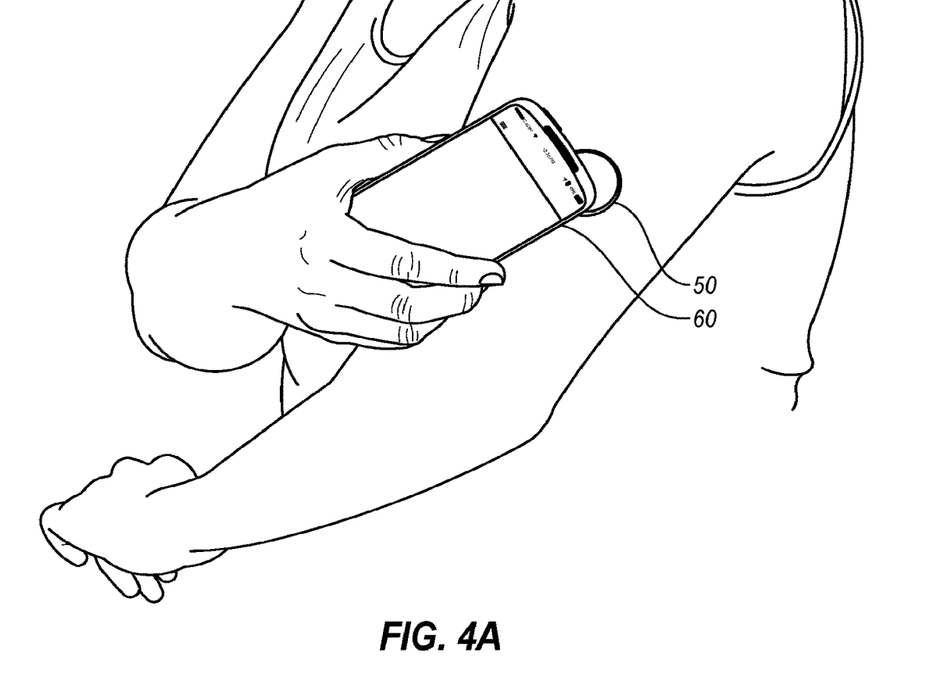
FIGS. 4A and 4B depict how data from a flash glucose monitor can be retrieved using a display device.
Figure 4B:
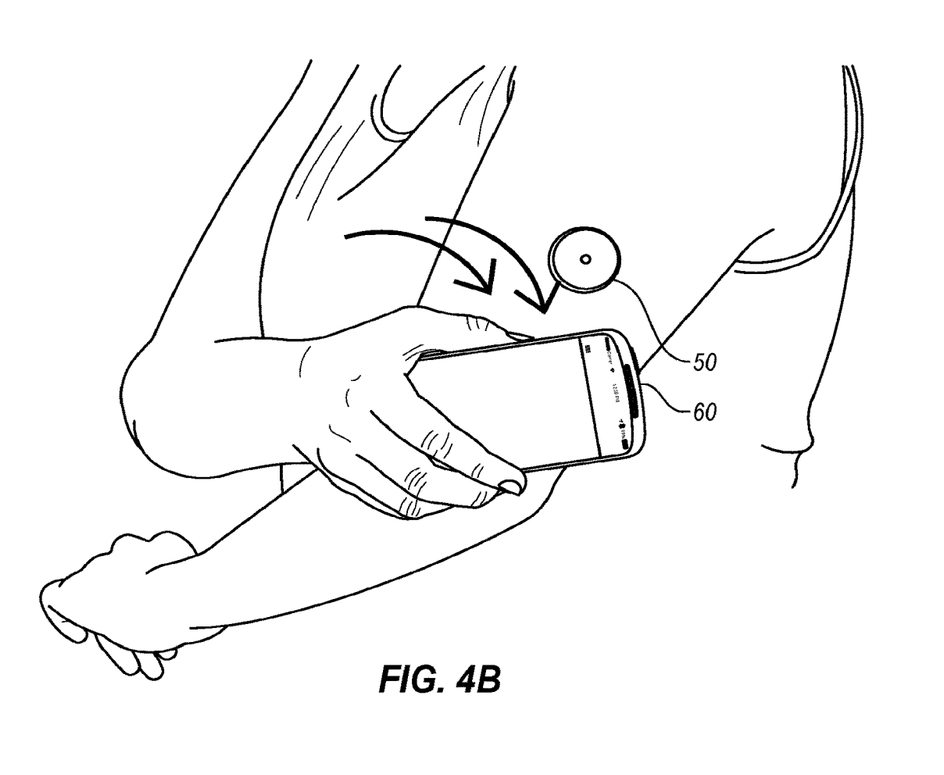
Figure 5A:
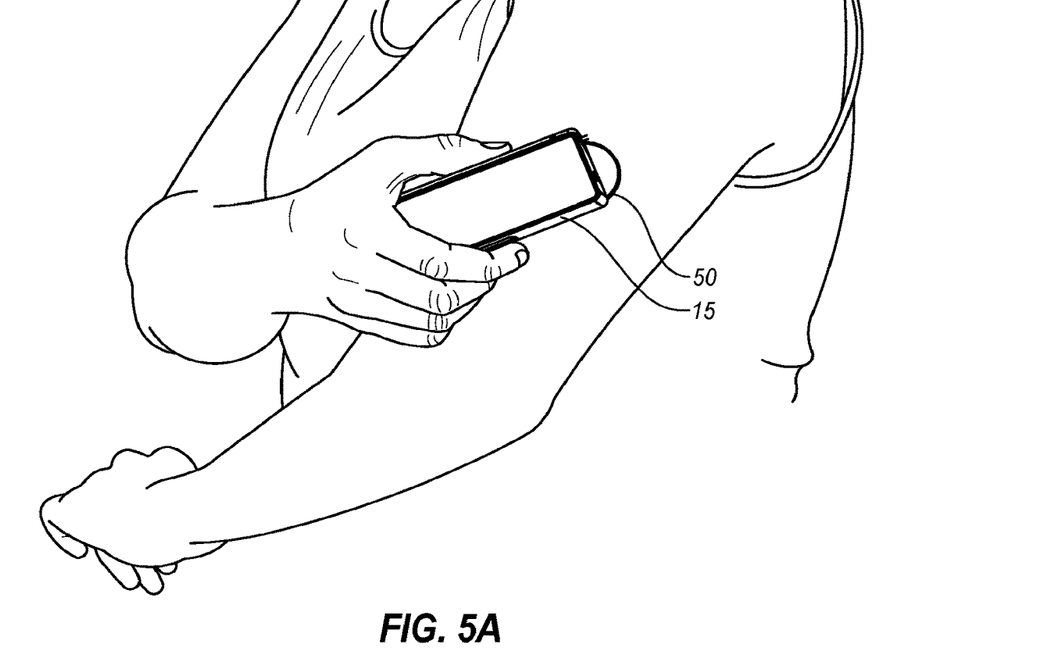
FIGS. 5A and 5B depict how data from a flash glucose monitor can be retrieved using a pump.
Figure 5B:
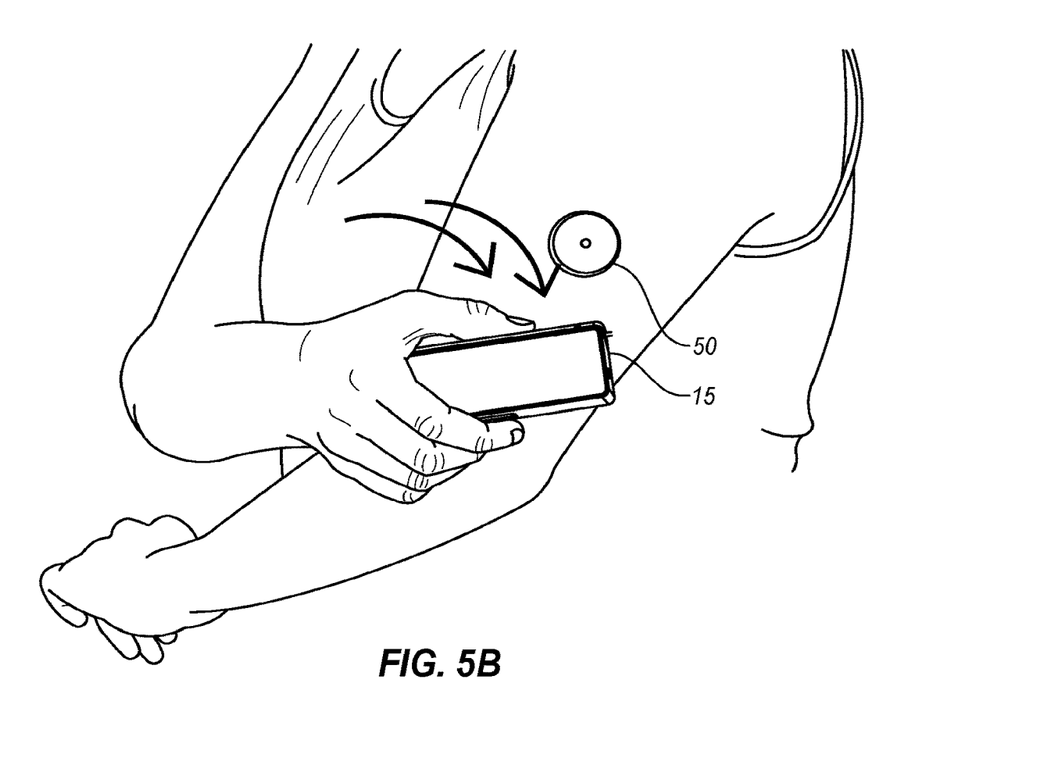
Figure 6A:
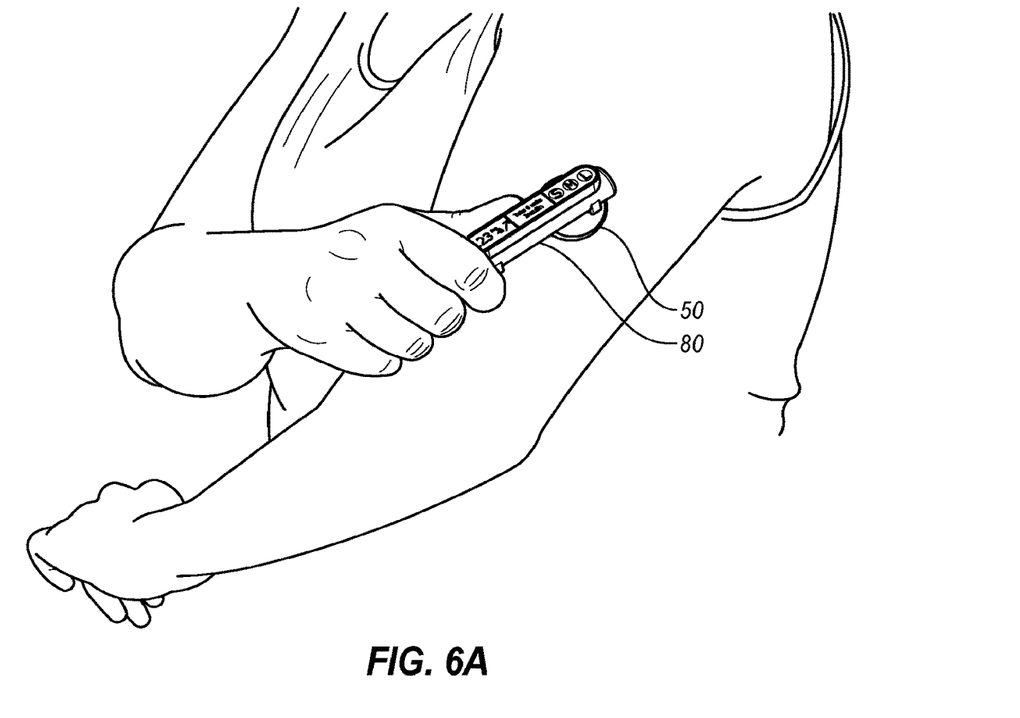
FIGS. 6A and 6B depict how data from a flash glucose monitor can be retrieved using a bolus administering device.
Figure 6B:
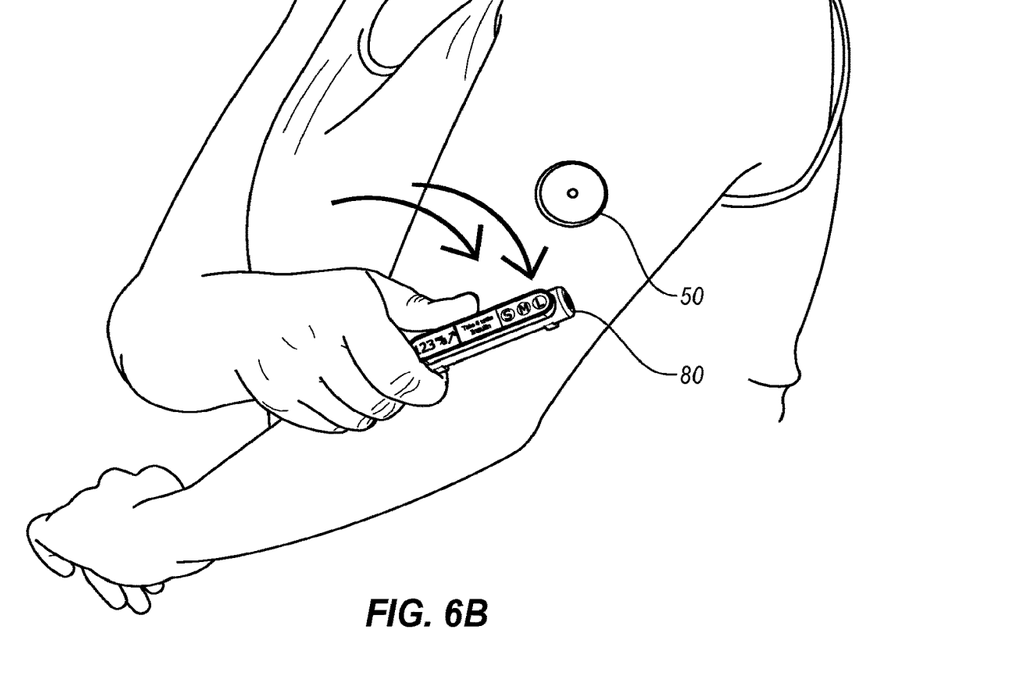

In some cases, the flash glucose monitor 50 may be invoked via near field communication (NFC) from one or more other components of diabetes management system 10. For example, the pump assembly 15 may communicate with the flash glucose monitor 50 via the wireless communication device 247 and/or an NFC device 248 communicating with the wireless communication device 54 of the flash glucose monitor 50. In these and other embodiments, as the pump assembly 15 is brought in physical proximity to the wireless communication device 247, the flash glucose monitor 50 may be invoked to provide the blood glucose readings to one or more of the devices within the system 10. An example of such invocation is illustrated in FIGS. 5A and 5B. As another example, a display device may include an NFC device 65 that may invoke the flash glucose monitor 50 when brought in physical proximity to the flash glucose monitor 50. An example of such invocation is illustrated in FIGS. 4A and 4B. As an additional example, a bolus administering device 80 may include a wireless communication device 85 that may invoke the flash glucose monitor 50 when brought in physical proximity to the flash glucose monitor 50. An example of such invocation is illustrated in FIGS. 6A and 6B.

Diabetes management system 10 may optionally include a blood glucose meter 70 (e.g., a glucose sensor). In some cases, blood glucose meter 70 can be in wireless communication with reusable pump controller 200. Blood glucose meter 70 can take a blood glucose measurement using one or more test strips (e.g., blood test strips). A test strip can be inserted into a strip reader portion of the blood glucose meter 70 and then receive the PWD's blood to determine a blood glucose level for the PWD. In some cases, the blood glucose meter 70 is configured to analyze the characteristics of the PWD's blood and communicate (e.g., via a BLUETOOTH® wireless communication connection, an NFC wireless communication, etc.) the information to reusable pump controller 200. In some cases, a user can manually input a glucose meter reading. The blood glucose meter 70 can be manually operated by a user and may include an output subsystem (e.g., display, speaker) that can provide the user with blood glucose readings that can be subsequently entered into the controller or user interface to collect the data from an unconnected BGM into the system. The blood glucose meter 70 may be configured to communicate data (e.g., blood glucose readings) obtained to reusable pump controller 200 and/or other devices, such as a display device 60. Such communication can be over a wired and/or wireless connection, and the data can be used by system 10 for a number of functions (e.g., calibrating the flash glucose monitor 50, confirming a reading from the flash glucose monitor 50, determining a more accurate blood glucose reading for a bolus calculation, detecting a blood glucose level when the flash glucose monitor 50 is malfunctioning, etc.).

In some cases, the system 10 can further include a control device. In some cases, the control device communicates wirelessly with other diabetes devices of system 10. The control device can be any of a variety of appropriate computing devices, such as the reusable pump controller 200, a processing capable iteration of the bolus administering device 80, a smartphone, a tablet computing device, a wearable computing device, a smartwatch, a fitness tracker, a laptop computer, a desktop computer, and/or other appropriate computing devices. In some cases (for example, where the reusable pump controller 200 does not determine a basal delivery rate), the control device can receive and log data from other elements of the system 10 and determine basal delivery rates using any method or approach, such as those described in U.S. patent application Ser. No. 15/601,282. In some cases, the basal delivery rate may be based at least in part on projected blood glucose levels. For example, the control device may predict future blood glucose levels based on historical readings, current JOB, expected delivery rate, etc. The control device may project and/or predict future blood glucose levels in any predictive manner, such as those described in U.S. patent application Ser. No. 15/601,282.

In some cases, a user can input relevant data into the control device. For example, the PWD may utilize the display device 60 to input relevant data into the control device via a wireless communication between the display device 60 and the control device. In some cases, the control device can be used to transfer data from the reusable pump controller 200 to another computing device (e.g., a back-end server or cloud-based device).

In some cases, the display device 60 provides a user interface (e.g., graphical user interface (GUI), speech-based user interface, motion-controlled user interface) through which users can provide information to control operation of the reusable pump controller 200, the control device, and/or any other component of the system 10. For example, the display device 60 can be a mobile computing device running a mobile app that communicates with reusable pump controller 200 over short-range wireless connections (e.g., BLUETOOTH® connection, Wi-Fi Direct connection, near-field communication (NFC) connection, etc.) to provide status information for the system 10 and allow a user to control operation of the system 10 (e.g., toggle between delivery modes, adjust settings, log food intake, change a fear of hypoglycemia index (FHI), confirm/modify/cancel bolus dosages, and the like). Additionally or alternatively, the display device 60 may provide an interface via which the PWD may observe various details or other piece of information related to the system 10. For example, the PWD may use the display device 60 to view historical blood glucose readings. As another example, the PWD may utilize the display device 60 to view messages from the controller.

The system 10 may include a bolus administering device 80 (e.g., a syringe, an insulin pen, a smart syringe with device communication capabilities, or the like) through which bolus dosages can be manually administered to a PWD. In some cases, a suggested dosage for a bolus to be administered using the bolus administering device 80 can be output to a user via the user interface of reusable pump controller 200 and/or the user interface of the display device 60. In some cases, the bolus administering device 80 can communicate through a wired and/or wireless connection with reusable pump controller 200 and/or the display device 60. In some cases, system 10 can allow users to input insulin deliveries made using a syringe or insulin pen. In some cases, the bolus administering device 80 may communicate with the flash glucose monitor 50 via a wireless communication device 85. The wireless communication device 85 may be configured to communicate over any modality, such as BLUETOOTH®, NFC, or any other wireless communication modality.

While one embodiment of a diabetes management system is illustrated in FIG. 1, it will be appreciated that any number, type, or style of diabetes management devices may be utilized in conjunction with the present disclosure. For example, a patch pump, a syringe, etc. may be utilized to enter doses of insulin delivered to a PWD.

Figure 2:
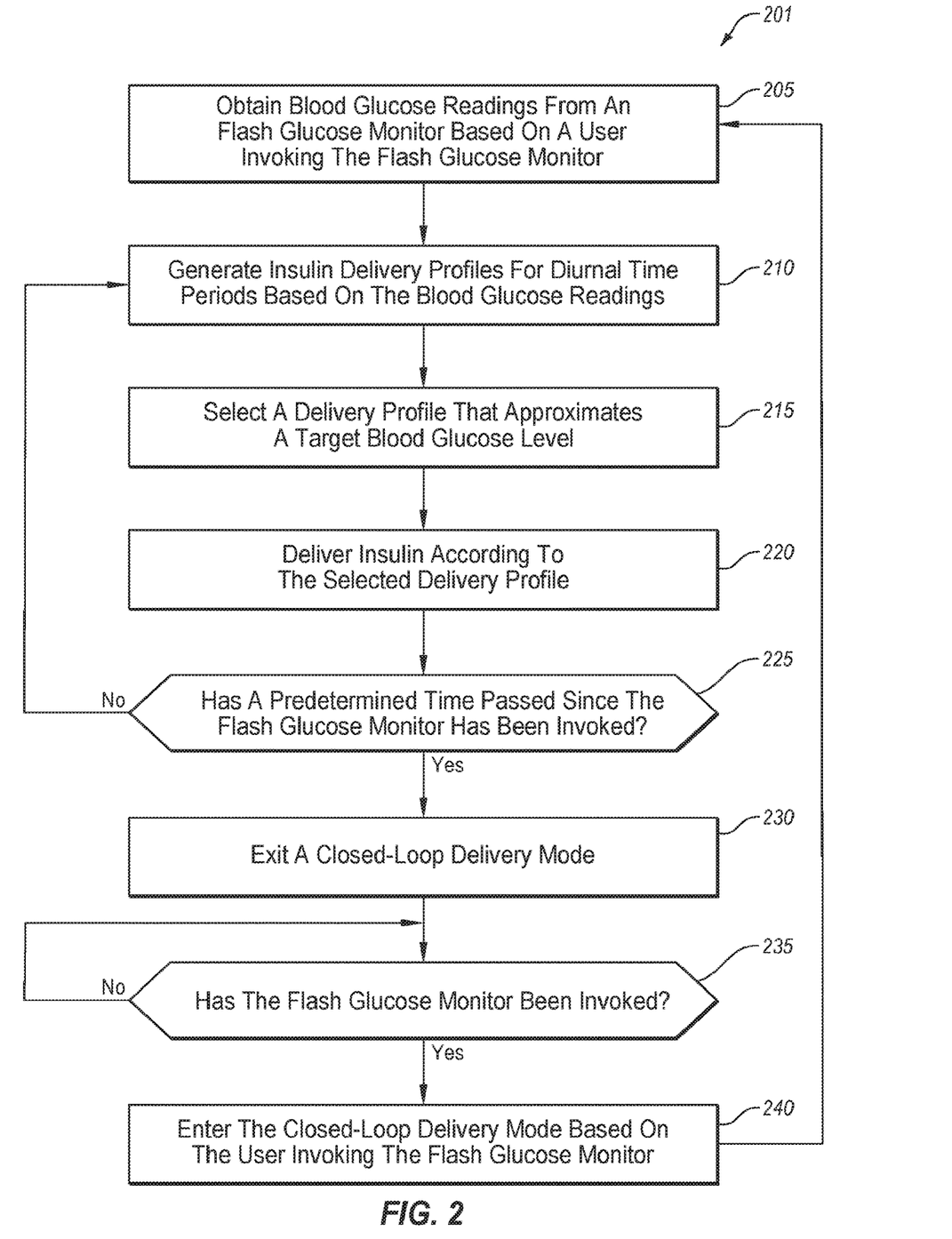
FIG. 2 illustrates a flowchart of an example method of providing insulin delivery based on user-initiated glucose readings.

Modifications, additions, or omissions may be made to FIG. 1 without departing from the scope of the present disclosure. For example, the system 10 may include any type or style of insulin delivery devices and/or monitoring devices. FIG. 2 illustrates a flow diagram of an example method 201 of providing insulin delivery based on user-initiated glucose readings, in accordance with one or more embodiments of the present disclosure. The method 201 may be performed by any suitable system, apparatus, or device.

For example, the system 10, the pump assembly 15, a processing capable version of the bolus administering device 80, the display device 60 of FIG. 1, and/or a remote server may perform one or more of the operations associated with the method 201. Although illustrated with discrete blocks, the steps and operations associated with one or more of the blocks of the method 201 may be divided into additional blocks, combined into fewer blocks, or eliminated, depending on the desired implementation.

At block 205, blood glucose readings may be obtained from a flash glucose monitor (flash glucose monitor) based on a user invoking the flash glucose monitor. For example, with reference to FIG. 1, a user may invoke the flash glucose monitor 50. Based on the user invoking the flash glucose monitor 50, the control device of a diabetes management system 10 may receive one or more blood glucose readings from the flash glucose monitor 50.

At block 210, delivery profiles may be generated of various delivery actions over one or more diurnal time segments based on the blood glucose readings obtained from the flash glucose monitor. For example, the delivery profiles may include a series of insulin delivery actions over time, where the delivery actions can include delivering a baseline basal rate, or delivering some ratio or multiple of the baseline basal rate, such as 0×, 1×, or 2× the baseline basal rate. In some cases the generation of the profiles may additionally include predicting how the various delivery profiles will affect the future blood glucose levels. Such prediction may be based on one or more user-specific diurnal-specific parameters such as BBR, ISF, CR, etc., for the diurnal time segments that fall within the projected delivery profile.

In some cases the delivery profiles and/or the predictions may be based on blood glucose readings obtained from the flash glucose monitor. For example, the flash glucose monitor may provide a current blood glucose reading and/or previous blood glucose readings against which previously predicted blood glucose levels can be compared. Additionally or alternatively, the trending of blood glucose levels may be projected out based on a known amount of insulin delivered and an estimated amount of insulin delivered by following the various delivery profiles.

At block 215, one of the delivery profiles may be selected based on the delivery profile approximating a target blood glucose level. In some cases, the delivery profile may most closely match the target blood glucose level among the generated delivery profiles. Such an approach of determining which delivery profile approximates the target blood glucose level may follow any approach, including a loss algorithm, etc.

At block 220, insulin may be delivered according to the selected profile. For example, a control device may provide instructions to an insulin delivery device (e.g., a pump) to deliver insulin according to a series of delivery actions of either 0×, 1×, or 2× the baseline basal rate over one or more diurnal time segments. The process of repeatedly generating delivery profiles, selecting a delivery profile, and delivering insulin based on the selected profile may be referred to as a closed-loop delivery mode as the insulin delivery is modified and adjusted based on the feedback loop of the blood glucose readings from the flash glucose monitor.

At block 225, a determination may be made whether a predetermined time has elapsed since the flash glucose monitor has been invoked by the user. For example, if the flash glucose monitor has not been invoked for three hours, the blood glucose readings may be stale and any predicted delivery profiles may not be as reliable as is desired. The predetermined time can be based on any of a variety of factors, including the duration of time the user has used a diabetes management system, the previous trends of the user, whether alternative blood glucose readings are available (e.g., from a BGM), etc. In these and other embodiments, the predetermined time may include thirty minutes, one hour, two hours, etc. If the predetermined time has elapsed without the user invoking the flash glucose monitor, the method 201 may proceed to the block 230. If the predetermined time has not elapsed, the method 201 may return to the block 210 to generate an additional set of delivery profiles, and continue to deliver insulin based on a selected delivery profile and based on any additional blood glucose readings obtained from the flash glucose monitor.

At block 230, a diabetes management system may exit a closed-loop delivery mode. For example, if the blood glucose readings from the flash glucose monitor are getting stale and the flash glucose monitor has not been invoked, the diabetes management system may transition into an open-loop delivery mode in which the insulin is delivered according to the BBR, rather than according to a personalized delivery profile. Stated another way, the system may transition so that the selected delivery profile is always 1× the BBR, rather than potentially delivering a different ratio or multiple of the BBR (e.g., 0×, or 2× the BBR).

At block 235, a determination may be made as to whether the flash glucose monitor has been invoked by the user. For example, the control device may monitor whether it has received any new or updated blood glucose readings from the flash glucose monitor. Additionally or alternatively, the control device may monitor whether the control device has received input from a user to invoke the flash glucose monitor via the control device. If the flash glucose monitor has been invoked, the method 201 may proceed to the block 240. If the flash glucose monitor has not been invoked, the method 201 may continue to monitor for invocation of the flash glucose monitor.

At block 240, the diabetes management system may enter the closed-loop delivery mode based on the user invoking the flash glucose monitor. For example, as illustrated in FIG. 2, the method may return to block 205 where additional blood glucose readings are obtained and additional delivery profiles are generated and selected. In some embodiments, the diabetes management system may wait until more than one blood glucose reading is obtained from the flash glucose monitor, such as two consecutive readings, etc. Additionally or alternatively, the number of new readings may be based on the duration of time the diabetes management system was in the open-loop delivery mode. For example, if the user fell asleep at 10 PM and did not invoke the flash glucose monitor until 8 AM the next morning (e.g., 10 hours without invoking the flash glucose monitor), the diabetes management system may wait to transition back to the closed-loop delivery mode until it has obtained three consecutive readings from the flash glucose monitor. As another example, if the user was on a two hour bike ride and did not invoke the flash glucose monitor, the diabetes management system may have transitioned to the open-loop delivery mode and may transition back to the closed-loop delivery mode immediately upon receiving updated blood glucose readings when the flash glucose monitor is invoked by the user.

In some cases, other prerequisites may be in place before transitioning back to the closed-loop delivery mode. For example, the diabetes management system may wait to transition to the closed-loop delivery mode until the diabetes management system receives a blood glucose level from a BGM, or may wait until a user invocation of a user interface, button, or other feature to direct the diabetes management system to change to the closed-loop delivery mode. Modifications, additions, or omissions may be made to the method 201 without departing from the scope of the present disclosure. For example, the operations of the method 201 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments.

Figure 3:
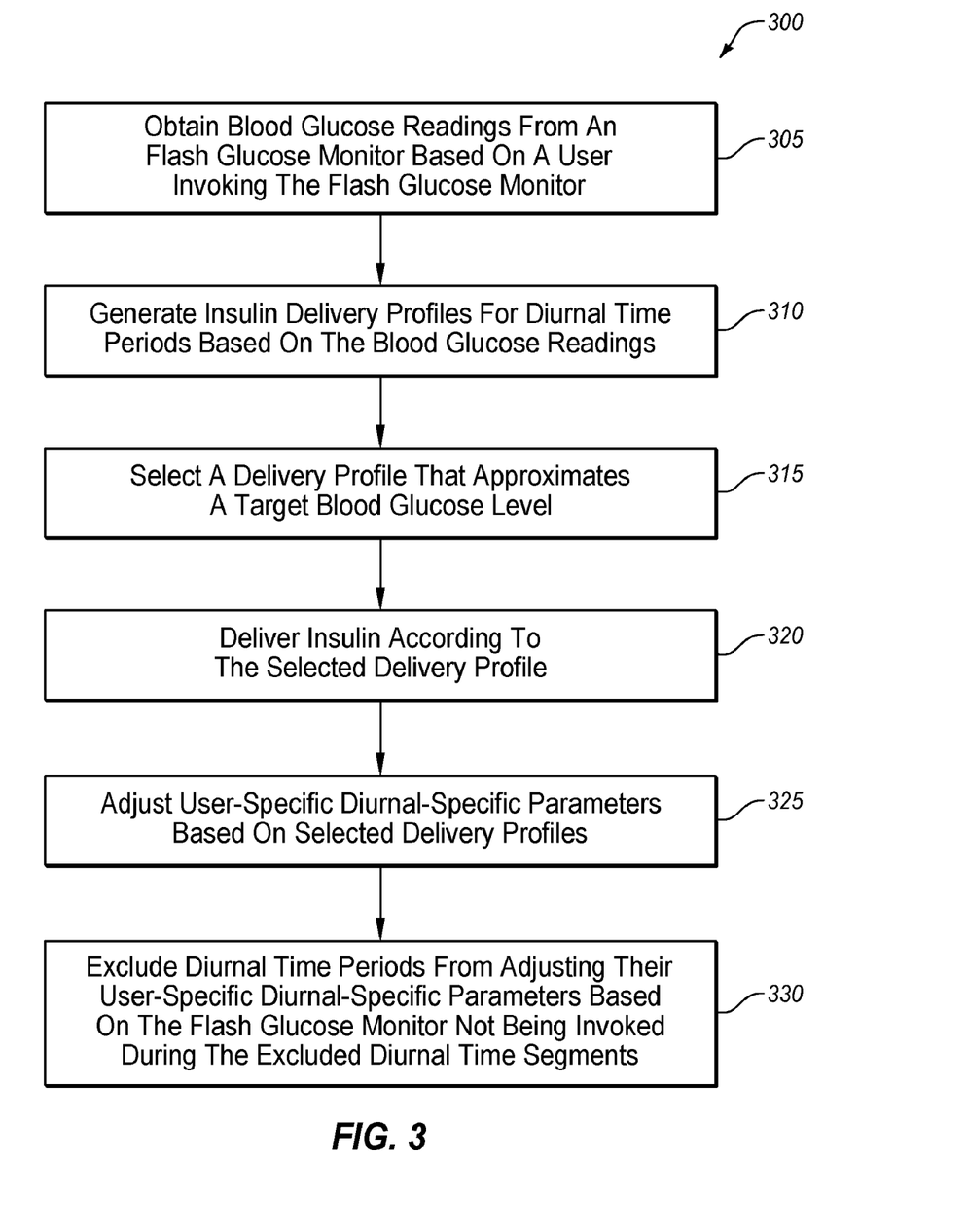
FIG. 3 illustrates a flowchart of another example method of providing insulin delivery based on user-initiated glucose readings.

FIG. 3 illustrates a flow diagram of an example method 300 of providing insulin delivery based on user-initiated glucose readings, in accordance with one or more embodiments of the present disclosure. The method 300 may be performed by any suitable system, apparatus, or device. For example, the system 10, the pump assembly 15, a processing capable version of the bolus administering device 80, the display device 60 of FIG. 1, and/or a remote server may perform one or more of the operations associated with the method 300. Although illustrated with discrete blocks, the steps and operations associated with one or more of the blocks of the method 300 may be divided into additional blocks, combined into fewer blocks, or eliminated, depending on the desired implementation.

At block 305, blood glucose readings may be obtained from a flash glucose monitor (flash glucose monitor) based on a user invoking the flash glucose monitor. The block 305 may be similar or comparable to the block 205 of FIG. 2.

At block 310, delivery profiles may be generated of various delivery actions over one or more diurnal time segments based on the blood glucose readings obtained from the flash glucose monitor. The block 310 may be similar or comparable to the block 210 of FIG. 2.

At block 315, one of the delivery profiles may be selected based on the delivery profile approximating a target blood glucose level. The block 315 may be similar or comparable to the block 215 of FIG. 2.

At block 320, insulin may be delivered according to the selected profile. The block 320 may be similar or comparable to the block 220 of FIG. 2.

At block 325, user-specific diurnal-specific parameters may be adjusted based on the delivery profiles selected at the block 315. In some cases, the block 325 may be performed at the end of the day, at the end of the week, etc., or at some other periodic interval. Such an adjustment may include adjusting parameters such as BBR, ISF, CR, etc., for one or more diurnal time segments. For example, if a diabetes management system delivered insulin at 2× the BBR for five days in a week between 10 AM and 11 AM, the block 325 may adjust the BBR during that time period for future days to be higher. Examples and additional description of such adjustments may be described with reference to U.S. application Ser. No. 15/601,282.

At block 330, one or more diurnal time segments may be excluded from the adjustment of block 325 based on the flash glucose monitor not being invoked during the one or more diurnal time segments. For example, at the end of a week, the diabetes management system may analyze the hours between 2 AM and 4 AM for a given week to determine if adjustments should be made to user-specific diurnal-specific parameters for the diurnal time segments corresponding to those two hours. The diabetes management system may identify that the flash glucose monitor was not invoked during those hours and so may not adjust the user-specific diurnal-specific parameters for the diurnal time segments associated with those two hours. In some cases, adjustments to the user-specific diurnal-specific parameters may be based on whether a base number of blood glucose readings were obtained during a diurnal time segment. For example, if a diurnal time segment spans one hour, the diabetes management system may not adjust the user-specific diurnal-specific parameters for that diurnal time segment unless there are at least two flash glucose monitor blood glucose readings during the diurnal time segment.

Modifications, additions, or omissions may be made to the method 300 without departing from the scope of the present disclosure. For example, the operations of the method 300 may be implemented in differing order. Additionally or alternatively, two or more operations may be performed at the same time. Furthermore, the outlined operations and actions are provided as examples, and some of the operations and actions may be optional, combined into fewer operations and actions, or expanded into additional operations and actions without detracting from the essence of the disclosed embodiments.

In some cases, the operations of the methods 201 of FIG. 2 and 300 of FIG. 3 may operate together. For example, during day to day delivery of insulin, the diabetes management system may deliver insulin based on a BBR and a selected delivery profile of multiple delivery profiles of various delivery actions of delivering a ratio or multiple of the BBR. The delivery profile selected may be based on projections based on the historic blood glucose levels obtained from the flash glucose monitor (e.g., the diabetes management system may operate in a closed-loop delivery mode). Additionally, the diabetes management system may adjust one or more of the user-specific diurnal-specific parameters. Using BBR as an example, for a diurnal time segment on a first day, the BBR may be delivering 1×, 1×, and 0× of the BBR of 0.1 U of insulin per hour, and for the diurnal time segment on a second day, the BBR may be delivering 1×, 1.5×, 1×, 1× of the BBR of 0.95 U of insulin per hour based on an adjustment to the BBR.

FIGS. 4A and 4B depict how data from a flash glucose monitor 50 can be retrieved using a display device 60. As illustrated in FIGS. 4A and 4B, the display device 60 (e.g., a smartphone) may be placed or swiped in physical proximity to the flash glucose monitor 50. Based on the display device 60 being in close physical proximity to the flash glucose monitor 50 (e.g., to facilitate near-field communications), the flash glucose monitor 50 may provide any stored blood glucose readings and/or may generate one or more new blood glucose readings. The blood glucose readings may be provided to the display device 60 or any other component of a diabetes management system (e.g., any of the components of the system 10 of FIG. 1).

FIGS. 5A and 5B depict how data from a flash glucose monitor 50 can be retrieved using a pump assembly 15. As illustrated in FIGS. 5A and 5B, the pump assembly 15 may be placed or swiped in physical proximity to the flash glucose monitor 50. Based on the pump assembly 15 being in close physical proximity to the flash glucose monitor 50 (e.g., to facilitate near-field communications), the flash glucose monitor 50 may provide any stored blood glucose readings and/or may generate one or more new blood glucose readings. The blood glucose readings may be provided to the pump assembly 15 or any other component of a diabetes management system (e.g., any of the components of the system 10 of FIG. 1).

FIGS. 6A and 6B depict how data from a flash glucose monitor 50 can be retrieved using a bolus administering device 80. As illustrated in FIGS. 6A and 6B, the bolus administering device 80 may be placed or swiped in physical proximity to the flash glucose monitor 50. Based on the bolus administering device 80 being in close physical proximity to the flash glucose monitor 50 (e.g., to facilitate near-field communications), the flash glucose monitor 50 may provide any stored blood glucose readings and/or may generate one or more new blood glucose readings. The blood glucose readings may be provided to the bolus administering device 80 or any other component of a diabetes management system (e.g., any of the components of the system 10 of FIG. 1).

The embodiments described herein may include the use of a special-purpose or general-purpose computer including various computer hardware or software modules, as discussed in greater detail below.

Embodiments described herein may be implemented using computer-readable media for carrying or having computer-executable instructions or data structures stored thereon. Such computer-readable media may be any available media that may be accessed by a general-purpose or special-purpose computer. By way of example, and not limitation, such computer-readable media may include non-transitory computer readable storage media including Random-Access Memory (RAM), Read-Only Memory (ROM), Electrically Erasable Programmable Read-Only Memory (EEPROM), Compact Disc Read-Only Memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable media.

Computer-executable instructions may include, for example, instructions and data, which cause a general-purpose computer, special-purpose computer, or special purpose processing device (e.g., one or more processors) to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the terms "module" or "component" may refer to specific hardware implementations configured to perform the operations of the module or component and/or software objects or software routines that may be stored on and/or executed by general-purpose hardware (e.g., computer-readable media, processing devices, etc.) of the computing system. In some embodiments, the different components, modules, engines, and services described herein may be implemented as objects or processes that execute on the computing system (e.g., as separate threads). While some of the system and methods described herein are generally described as being implemented in software (stored on and/or executed by general-purpose hardware), specific hardware implementations or a combination of software and specific hardware implementations are also possible and contemplated. In the present description, a "computing entity" may be any computing system as previously defined herein, or any module or combination of modulates running on a computing system.

Any ranges expressed herein (including in the claims) are considered to be given their broadest possible interpretation. For example, unless explicitly mentioned otherwise, ranges are to include their end points (e.g., a range of "between X and Y" would include X and Y). Additionally, ranges described using the terms "substantially," "approximately," or "about" are to be understood to be given their broadest meaning consistent with the understanding of those skilled in the art. Additionally, the term approximately includes anything within 10%, 5%, or 1%, or within manufacturing or typical tolerances.

While certain embodiments have been described and shown in the accompanying drawings, such embodiments are merely illustrative and not restrictive of the scope of the disclosure, and this disclosure is not limited to the specific constructions and arrangements shown and described, since various other additions and modifications to, and deletions from, the described embodiments will be apparent to one of ordinary skill in the art. Thus, the scope of the disclosure is only limited by the literal language, and legal equivalents, of the claims that follow.

What is claimed is:

1. A method of insulin delivery, the method comprising:
    obtaining one or more blood glucose readings from a flash glucose monitor, the blood glucose readings obtained in response to a user invocation of the flash glucose monitor;
    generating a plurality of insulin delivery profiles of insulin delivery actions over a plurality of diurnal time segments based on the one or more blood glucose readings;
    selecting one of the plurality of insulin delivery profiles that is projected to approximate a target blood glucose level; and
    providing the selected delivery profile to be utilized with an insulin delivery device to deliver the selected delivery profile to the user.

2. The method of claim 1, further comprising adjusting one or more user-specific diurnal-specific parameters based on the selected delivery profile.

3. The method of claim 2, further comprising excluding one or more diurnal time segments from having associated user-specific diurnal-specific parameters adjusted based on the flash glucose monitor not being invoked during the one or more excluded diurnal time segments.

4. The method of claim 1, further comprising receiving the one or more blood glucose monitor readings from the flash glucose monitor in response to the user invoking the flash glucose monitor.

5. The method of claim 1, further comprising exiting a closed-loop delivery mode such that the selected delivery profile delivers a predetermined baseline basal rate based on a predetermined period of time elapsing without invocation of the flash glucose monitor.

6. The method of claim 1, further comprising entering a closed-loop delivery mode based on the user invoking the flash glucose monitor.

7. The method of claim 6, wherein the closed-loop delivery mode is one of a hybrid closed-loop mode and a full closed-loop mode.

8. The method of claim 1, further comprising delivering insulin according to the selected delivery profile with the insulin delivery device.

9. A method of insulin delivery, the method comprising:
    obtaining one or more blood glucose readings from a flash glucose monitor, the blood glucose readings obtained in response to a request of the flash glucose monitor;

generating a plurality of insulin delivery profiles of insulin delivery actions over a plurality of diurnal time segments based on the one or more blood glucose readings;

selecting one of the plurality of insulin delivery profiles that is projected to approximate a target blood glucose level; and providing the selected delivery profile to be utilized with an insulin delivery device to deliver the selected delivery profile to a user.

10. An insulin delivery system comprising:

an insulin delivery device configured to deliver insulin to a user;

a flash glucose monitor configured to obtain one or more blood glucose readings from the user; and a controller configured to perform or control performance of operations, the operations comprising:

obtaining one or more blood glucose readings from the flash glucose monitor;

generating a plurality of insulin delivery profiles of insulin delivery actions over a plurality of diurnal time segments based on the one or more blood glucose readings;

selecting one of the plurality of insulin delivery profiles that is projected to approximate a target blood glucose level; and     providing the selected delivery profile to be utilized with the insulin delivery device to deliver a least a portion of the selected delivery profile to the user.

11. The system of claim 10, wherein the operations further comprise delivering insulin according to the selected delivery profile with the insulin delivery device.

12. The system of claim 10, wherein the insulin delivery device comprises an insulin pump assembly configured to supply an at least partially continuous subcutaneous insulin infusion therapy to the user.

13. The system of claim 10, wherein the insulin delivery device comprises a bolus administering device configured to supply discrete insulin doses to the user.

14. The system of claim 13, wherein the bolus administering device comprises an insulin pen.

15. The system of claim 10, wherein the controller is integrated with the insulin delivery device.

16. The system of claim 10, wherein the controller comprises a separate device from the insulin delivery device.

17. The system of claim 16, wherein the separate device of the controller is configured to communicate with the insulin delivery device to provide the selected delivery profile.

18. The system of claim 10, wherein the controller is configured to enable a user to at least one of modify or input data relating to the selected delivery profile.

19. The system of claim 10, the flash glucose monitor is configured to provide the blood glucose readings in response to a user request of the flash glucose monitor.

20. The system of claim 19, the flash glucose monitor is configured to be invoked via near field communication (NFC) by the user.

* * * * *

UNITED STATES PATENT AND TRADEMARK OFFICE
CERTIFICATE OF CORRECTION

PATENT NO. : 10,610,644 B2  
APPLICATION NO. : 15/870686  
DATED : April 7, 2020  
INVENTOR(S) : Bryan Mazlish and Lane Desborough Page 1 of 1

It is certified that error appears in the above-identified patent and that said Letters Patent is hereby corrected as shown below:

In the Specification  
Column 11, Line 66, change "current JOB," to --current IOB,--

Signed and Sealed this  
Twentieth Day of April, 2021

Drew Hirshfeld  
*Performing the Functions and Duties of the*  
*Under Secretary of Commerce for Intellectual Property and*  
*Director of the United States Patent and Trademark Office*